US00PP17610P2

(12) United States Plant Patent
Oudshoorn

(10) Patent No.: US PP17,610 P2
(45) Date of Patent: Apr. 17, 2007

(54) ***PAPAVER* PLANT NAMED 'MISS PIGGY'**

(50) Latin Name: *Papaver orientale*
Varietal Denomination: Miss Piggy

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/248,827

(22) Filed: Oct. 12, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Papaver* plant named 'Miss Piggy', characterized by its upright plant habit; moderately vigorous growth habit; freely flowering habit; semi-double flowers with fringed and light pink-colored petals; and strong peduncles.

1 Drawing Sheet

Botanical designation: *Papaver orientale.*
Cultivar denomination: 'Miss Piggy'.

BACKGROUND OF THE INVENTION

The present Invention relates to a new and distinct cultivar of *Papaver* plant, botanically known as *Papaver orientale,* commercially referred to as Oriental Poppy, and hereinafter referred to by the cultivar name Miss Piggy.

The new *Papaver* is a product of a planned breeding program conducted by the Inventor in Rijpwetering, The Netherlands. The objective of the breeding program is to develop new *Papaver* cultivars with compact plant habit and numerous flowers.

The new *Papaver* originated from a cross-pollination made by the Inventor in 1999 of two unnamed selections of *Papaver orientale,* not patented. The new *Papaver* was discovered and selected as a single plant by the Inventor in 2000 in a controlled environment in Rijpwetering, The Netherlands, from the resultant progeny of the stated cross-pollination.

Asexual reproduction of the new cultivar by cuttings at Rijpwetering, The Netherlands since 2001, has shown that the unique features of this new *Papaver* are stable and reproduced true to type in successive generations.

SUMMARY OF THE INVENTION

Plants of the cultivar Miss Piggy have not been observed under all possible environmental conditions. The phenotype may vary somewhat with variations in environment such as temperature and light intensity without, however, any variance in genotype.

The following traits have been repeatedly observed and are determined to be the unique characteristics of 'Miss Piggy'. These characteristics in combination distinguish 'Miss Piggy' as a new and distinct *Papaver* cultivar:

1. Upright plant habit.
2. Moderately vigorous growth habit.
3. Freely flowering habit.

4. Semi-double flowers with fringed and light pink-colored petals.
5. Strong peduncles.

Plants of the cultivar Miss Piggy differ from plants of the parent selections primarily in flower form.

Plants of the new *Papaver* can also be compared to plants of the *Papaver* cultivar Elizabeth, not patented. In side-by-side comparisons conducted in Rijpwetering, The Netherlands, plants of the new *Papaver* differed from plants of the cultivar Elizabeth in the following characteristics:

1. Plants of the new *Papaver* had stronger peduncles than plants of the cultivar Elizabeth.
2. Plants of the new *Papaver* and the cultivar Elizabeth differed in flower form.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Papaver.*

The photograph at the top of the sheet comprises a side perspective view of typical plants grown in an outdoor nursery.

The photograph in the center of the sheet is a close up view of a typical flower of 'Miss Piggy'.

The photograph at the bottom of the sheet is a close-up view of a typical leaf of 'Miss Piggy'.

DETAILED BOTANICAL DESCRIPTION

In the following description, color references are made to The Royal Horticultural Society Colour Chart, 2001 Edition, except where general terms of ordinary dictionary significance are used. Plants used for the abovementioned photographs and following observations and measurements were grown in an outdoor nursery in Lisserbroek, The Netherlands, and under conditions which closely approximate commercial production conditions during the spring.

The photographs, measurements and observations were taken in May when the plants were about two years old. During this time, day temperatures ranged from 14° C. to 27° C. and night temperatures ranged from 5° C. to 12° C.

Botanical classification: *Papaver orientale* cultivar Miss Piggy.

Parentage:

*Female, or seed, parent.*—Unnamed selection of *Papaver orientale,* not patented.

*Male, or pollen, parent.*—Unnamed selection of *Papaver orientale,* not patented.

Propagation:

*Type.*—By cuttings.

*Time to develop roots.*—About 90 days at 18° C.

*Root description.*—Fleshy, thick; light brown in color.

Plant description:

*Form.*—Herbaceous perennial flowering plant; mostly upright; narrow inverted triangle. Basally branching, rosette; flowering stems arise from the base. Moderately vigorous.

*Plant height.*—About 74 cm.

*Plant diameter.*—About 78 cm.

*Foliage description.*—Arrangement: Alternate; simple. Shape: Lanceolate, pinnately and deeply dissected. Length: About 36.8 cm. Width: About 18.3 cm. Leaf segment shape: Lanceolate; mid-section and base, pinnatisect; apex, pinnatifid. Leaf segment apex: Acute. Leaf segment base: Cuneate. Leaf segment margin: Serrate; occasionally biserrate. Texture, upper and lower surfaces: Pubescent; rough. Venation pattern: Pinnate. Color: Developing foliage, upper and lower surfaces: 143A. Fully expanded foliage, upper surface: Between 137A and 143A. Fully expanded foliage, lower surface: 137C. Venation, upper surface: 144D. Venation, lower surface: 144A to 144C. Petioles: Length: About 14 cm. Diameter: About 8 mm. Color: 144B to 144C.

Flower description:

*Flower type and habit.*—Single rotate flowers; flowers terminal and face mostly upright. Flowers not persistent. One flower per flowering stem, about six flowers per plant.

*Natural flowering season.*—Plants flower continuously from mid-May to mid-June in The Netherlands.

*Fragrance.*—Faint, sweet.

*Flower longevity on the plant.*—About three days.

*Flower size.*—Diameter: About 15.4 cm. Depth (height): About 8.5 cm.

*Flower buds.*—Length: About 4.5 cm. Diameter: About 3.4 cm. Shape: Narrowly oblong. Texture: Pubescent; rough. Color: 143A.

*Petals.*—Arrangement/appearance: Rotate; about seven petals in two whorls forming a cup-shaped corolla. Length: About 9.5 cm. Width: About 11.4 cm. Shape: Broadly obcordate. Apex: Irregularly incised; ruffled. Margin: Entire; ruffled. Texture, upper and lower surfaces: Smooth; glabrous. Color: When opening and fully opened, upper surface: Lighter than 49D; towards the base, 59B to 59D. When opening and fully opened, lower surface: Lighter than 49D; towards the base, between 53A and 59B.

*Sepals.*—None observed.

*Flower bracts.*—Quantity per flower: Four. Length: About 6.5 cm. Width: About 5.1 cm. Shape: Pinnatisect; apex, acute; margins, serrate. Texture, upper and lower surfaces: Pubescent. Color, upper surface: 143A. Color, lower surface: 138A.

*Flowering stems* (*peduncles*).—Length: About 65.5 cm. Diameter: About 1 cm. Internode length: About 12.4 cm. Strength: Strong. Aspect: Erect. Texture: Pubescent; rough. Color: 144B to 144C.

*Reproductive organs.*—Stamens: Quantity per flower: Numerous, typically about 300. Stamen length: About 1.7 cm. Anther shape: Narrowly oblong; basifixed. Anther length: About 3 mm. Anther color: 200A. Filament length: About 1.7 cm. Filament color: N186C; towards the base, N186D. Pollen amount: Abundant. Pollen color: N186A to 202A. Pistils: Quantity per flower: About 15. Pistil length: About 8 mm. Stigma shape: Narrowly oblong, flat. Stigma color: N186A to N186B to 184B. Ovary color: 144B.

*Fruits.*—Quantity per flower: One. Type: Capsule. Length: About 2.3 cm. Diameter: About 3 cm. Color: 136A to 137A.

*Seeds.*—Quantity per fruit: About 900. Length: About 1 mm. Diameter: About 1 mm. Color: Closest to 202A to 202B.

Disease/pest resistance: Plants of the new *Papaver* have been noted to be resistant to pathogens and pests common to *Papaver.*

Temperature tolerance: Plants of the new *Papaver* have been observed to tolerate temperatures from −20° C. to 30° C.

It is claimed:

1. A new and distinct cultivar of *Papaver* plant named 'Miss Piggy', as illustrated and described.

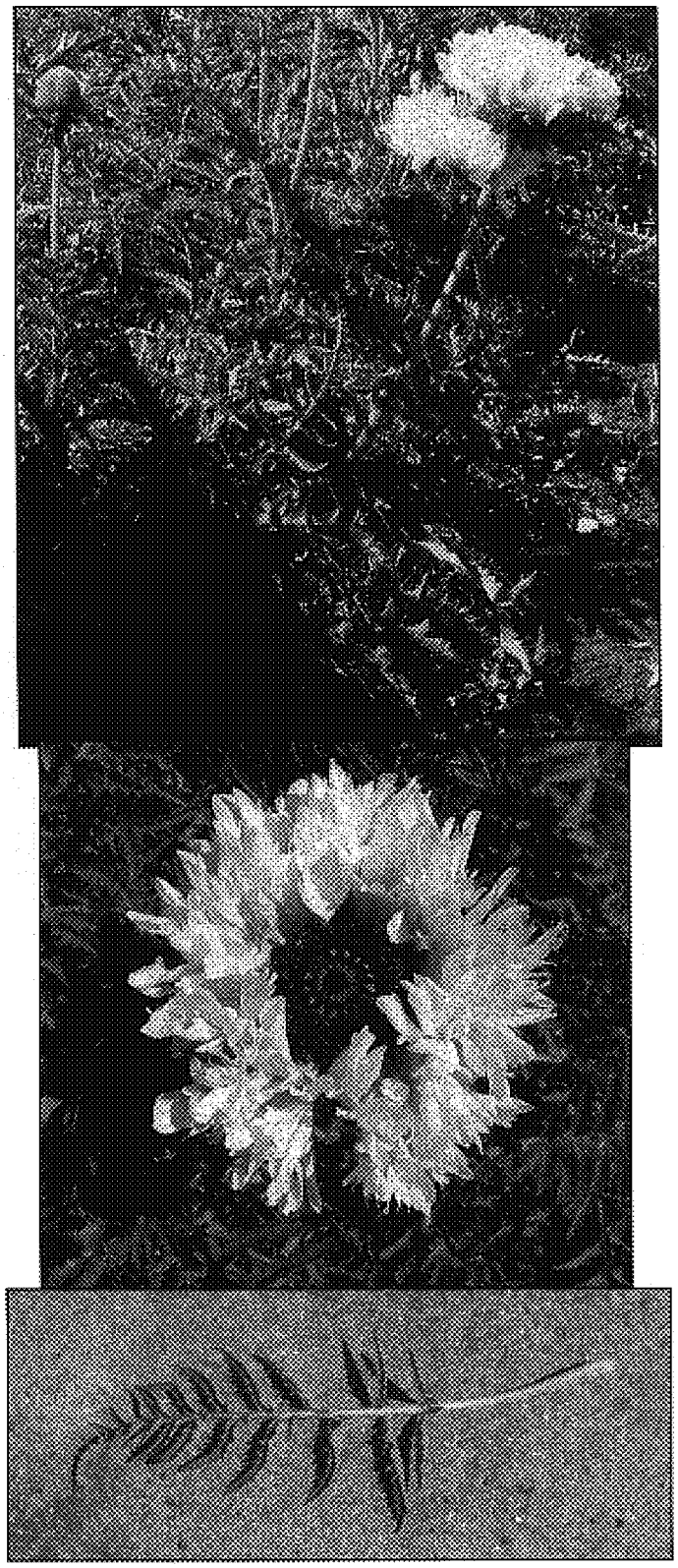

* * * * *